United States Patent [19]

Cousse et al.

[11] E Re. 31,237

[45] Reissued May 10, 1983

[54] 2-BENZOYL-4-NITROANILIDES AND THEIR USE AS MEDICAMENTS

[75] Inventors: Henri Cousse; Gilbert Mouzin, both of Castres, France

[73] Assignee: Pierre Fabre S.A., Paris, France

[21] Appl. No.: 350,233

[22] Filed: Feb. 19, 1982

Related U.S. Patent Documents

Reissue of:

[64] Patent No.: 4,289,770
Issued: Sep. 15, 1981
Appl. No.: 159,070
Filed: Jun. 13, 1980

[30] Foreign Application Priority Data

Jun. 25, 1979 [FR] France ..... 79 16213

[51] Int. Cl.[3] ..... A61K 31/535; A61K 31/16; C07C 103/183; C07D 295/14

[52] U.S. Cl. ..... 424/248.54; 424/250; 424/324; 544/167; 544/397; 564/189; 564/190; 564/191; 564/195

[58] Field of Search ..... 544/167, 397; 564/189, 564/190, 191, 195; 424/248.54, 250, 324

[56] References Cited

U.S. PATENT DOCUMENTS 3,772,371 11/1973 Tachikawa et al. ..... 564/195
3,906,003 9/1975 Akatsu et al. ..... 564/195

*Primary Examiner*—Robert W. Ramsuer
*Attorney, Agent, or Firm*—Gordon W. Hueschen

[57] ABSTRACT

New derivatives of 2-benzoyl-4-nitro anilides, their preparation and their use as medicaments.

The new chemical derivatives of the invention have the general formula

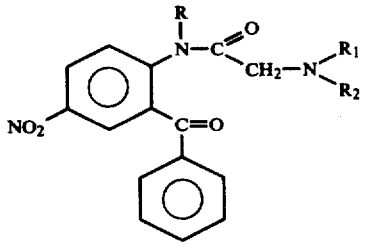

in which

R represents a linear or branched alkyl group, an alkenyl group, a cycloalkyl group or a benzyl group, $R_1$ represents a hydrogen atom, an alkyl group or a hydroxy alkyl group, $R_2$ represents a hydroxy-alkyl, alkenyl or alkynyl group, possibly substituted one or more times by an alkyl radical, or a cycloalkyl group having three to six carbon atoms;

$R_1$ and $R_2$ may furthermore form, with the nitrogen atom to which they are attached, a nitrogen heterocycle containing possibly a second heteroatom selected from among oxygen and nitrogen;

under the condition, however, that when $R_2$ represents a hydroxy-alkyl group $R_1$ may not be a hydrogen atom.

Use as hypnotic agents for the treatment of insomnia.

6 Claims, No Drawings

2-BENZOYL-4-NITROANILIDES AND THEIR USE AS MEDICAMENTS

Matter enclosed in heavy brackets [ ] appears in the original patent but forms no part of this reissue specification; matter printed in italics indicates the additions made by reissue.

The present invention, developed at the Pierre FABRE Research Center, concerns new chemical compounds derived from 2-benzoyl-4-nitroanilides, their method of preparation and their use in therapy.

The chemical compounds which are the object of the present invention are represented by general formula I:

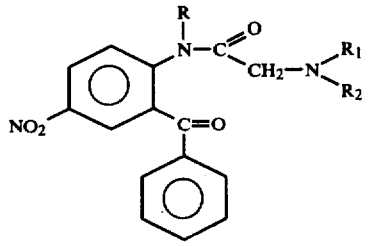

(I)

in which:

R represents a linear or branched alkyl group or an alkenyl, cycloalkyl or benzyl group;

$R_1$ represents a hydrogen atom or an alkyl or hydroxyalkyl group;

$R_2$ represents a hydroxyalkyl, alkenyl, or alkynyl group, possibly substituted one or more times by an alkyl radical, or a cycloalkyl group having 3 to 6 carbom atoms;

$R_1$ and $R_2$ may furthermore form, with the nitrogen atom to which they are bound, a nitrogen heterocycle, possibly including a second heteroatom selected from among oxygen and nitrogen.

The present invention also applies to salts of compounds of formula I obtained with therapeutically acceptable inorganic or organic acids.

The present invention also relates to a method of preparing compounds of formula I which are characterized by condensing a compound of general formula II:

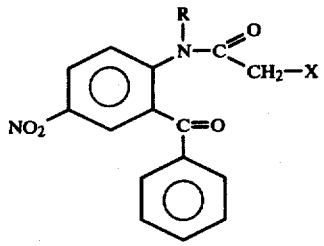

(II)

in which

R has the meaning given in connection with general formula I, and

X represents a halogen atom; with an amine of general formula III

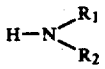

(III)

in which $R_1$ and $R_2$ have the meaning given in connection with general formula I.

The products of general formula II may be prepared by one of the two following methods:

Method a:

from 2-halo-5nitro-benzophenone

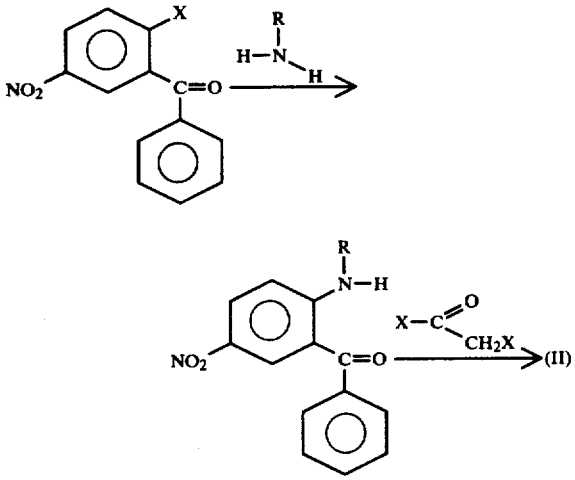

Method b:

from 2-amino-5-nitro-benzophenone

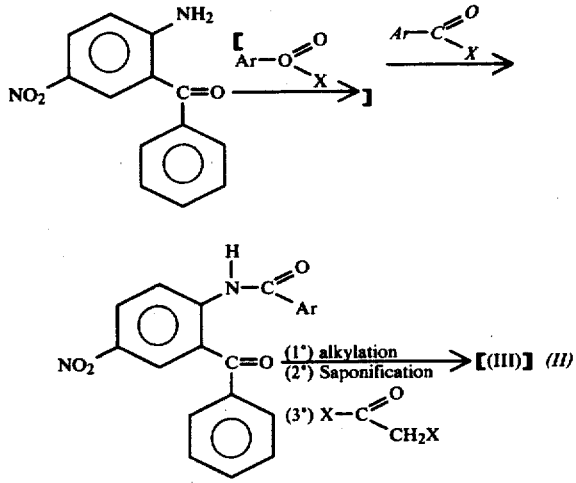

X and R having the meanings given above.

The present invention finally relates to the use of the compounds of general formula I as medicaments which are active on the central nervous system and in particular as hypnotics.

The present invention will be described below in further detail in connection with the following nonlimitative examples:

EXAMPLE 1

Hydrochloride of N-methyl-2'-benzoyl-4'-nitro-2-morpholino acetanilide

(A) Preparation of 2-methylamino-5-nitro-benzophenone

Method a:

To a suspension of 2.61 g (0.01 mol) of 2-chloro-5-nitro-benzophenone in 20 cc of ethanol of 95° GL there are added 7.75 cc (0.1 mol) of 40% methylamine in water, and then 0.15 g of cuprous chloride and 0.15 g of powdered copper. After heating for five hours at 60° C., the suspension is evaporated to dryness and the residue is absorbed by a 1 N solution of hydrochloric acid.

Extraction is effected with ethyl acetate followed by washing with water until neutral and drying over sodium sulfate. Upon recrystallization from a mixture of ethyl acetate and hexane (75:25) there are obtained 2.28 g of yellow crystals. Melting point 168° C. Yield about 90%.

Slab chromatography:

support: silica gel 60 F 254 Merck; solvent: ethyl acetate-petroleum ether 30:70; development: UV and iodine; Rf: 0.73.

Method b:

A suspension of 11.07 g (0.031 mol) of 2-benzamido-5-nitro benzophenone and 724 mg (0.003 mol) of benzyltriethyl ammonium chloride is heated to 60° C. in 450 cc of toluene. 16 cc of 10 N caustic soda (0.16 mol) and 10 cc of methyl sulfate (0.1 mol) in 50 cc of toluene are added simultaneously drop by drop. The reaction mixture is maintained under strong agitation at 60° C. for 8 hours. After return to room temperature, it is diluted and allowed to settle. The organic phase is evaporated and the residue absorbed by 200 cc of ethanol and 60 cc of 6 N caustic soda (0.36 mol). After heating for two hours at 70° C., the ethanol is evaporated, the residue is absorbed by ethyl acetate, washed with water and dried over sodium sulfate. Upon recrystallization from a mixture of ethyl acetate and hexane (75:25), there are recovered 7.22 g of yellow crystals. Melting point 168° C. Yield 88%.

(B) Preparation of N-methyl-2'-benzoyl-4'-nitro-2-bromo acetanilide

To a suspension of 2.56 g (0.01 mol) of 2- methylamino-benzophenone in 100 cc of toluene there is added 1.05 cc (0.012 mol) of bromacetyl choride and the reaction mixture is heated for 8 hours at 100° C.

It is allowed to return to room temperature, whereupon an iced solution of 5 g of sodium carbonate in 100 cc of water is added and agitation is effected for 15 minutes. It is allowed to settle; the organic phase is washed with water until neutral and dried over sodium sulfate. It is filtered and the organic phase evaporated; the residual oil obtained is crystallized by trituration in ether. 2.85 g of beige-colored crystals are recovered. Melting point 95° C. Yield: 76%.

Slab chromatography:

support: silica gel 60 F 254 Merck; solvent: ethyl acetate-petroleum ether 30:70; development: UV and iodine; Rf: 0.44.

(C) Preparation of N-methyl-2'-benzoyl-4'-nitro-2-morpholino-acetanilide hydrochloride To a solution of 3.77 g (0.01 mol) of N-methyl-2'-benzoyl-4'-nitro-2-bromo acetanilide in 30 cc of methylene chloride, 2.6 cc (0.03 mol) of morpholine are rapidly added. The reaction mixture is maintained under vigorous agitation for four hours at room temperature and then refluxed for one hour. It is extracted twice with 3 N hydrochloric acid; the aqueous phases are treated with sodium bicarbonate and then extracted with ethyl acetate.

It is washed with water until neutral and dried over sodium sulfate. It is decolorized by means of animal black. After filtration and evaporation of the solvent, there is obtained a residual oil which is treated with a saturated ethanolic solution of hydrochloric acid.

The hydrochloride formed is precipitated by addition of ether and by recrystallization from a mixture of methanol and isopropyl ether. There is recovered, in a yield of 82%, a product having the formula:

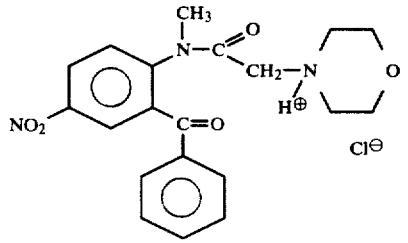

Empirical formula: $C_{20}H_{22}ClN_3O_5$; Molecular weight: 419.87; Crystals: Slightly colored white; Melting point: 170° C.; IR spectrum (KBr) $\nu$ $cm^{-1}$: 1679–1655 and 1612.

Slab chromatography.

support: silica gel 60 F 254 Merck; solvent: methanol-chloroform 15.85; development: UV and iodine; Rf: 0.68.

Solubilities: Insoluble in water. 2.5% soluble in DMSO and 10% soluble in methylpyrrolidone.

EXAMPLE 2

Acid maleate of N-ethyl-2'-benzoyl-4'-nitro-2-morpholino-acetanilide

(A) Preparation of 2-ethylamino-5-nitrobenzophenone

In a manner similar to that described in Example 1(A), but with the use of ethylamine, there is obtained 2-ethylamino-5-nitrobenzophenone in a yield of 90%. Melting point: 135° C. Yellow crystals.

Slab chromatography:

support: silica gel 60 F 254 Merck; solvent: ethyl acetate-petroleum ether 10:90; development UV and iodine; Rf: 0.30.

(B) Preparation of N-ethyl-2'-benzoyl-4'-nitro-2-bromo acetanilide

In a manner similar to that described in Example 1(B) but using 2-ethylamino-5-nitrobenzophenone, N-ethyl-2'-benzoyl-4'-nitro-2-bromo acetanilide is recovered in a yield of 95%. White crystals. Melting point: 95° C.

Slab chromatography:

support: silica gel 60 F 254 Merck; solvent: ethyl acetate-petroleum ether 30:70; development: UV and iodine; Rf: 0.40.

(C) Preparation of acid maleate of N-ethyl-2'-benzoyl-4'-nitro-2-morpholino acetanilide In a manner similar to that described in Example 1(C), but using N-ethyl-2'-benzoyl-4'-nitro-2-bromo acetanilide and maleic acid as salifying agent, there is obtained, in a yield of 87%, the product of the formula:

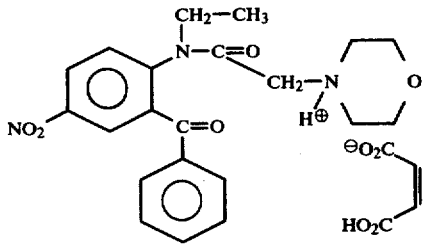

Empirical formula: $C_{25}H_{27}N_3O_9$; Molecular weight: 513.49; White crystals; Melting point: 165° C.

Slab chromatography:

support: silica gel 60 F 254 Merck; solvent: ethyl acetate; development: UV and iodine; Rf: 0.24.

EXAMPLE 3

Acid maleate of N-propyl-2'-benzoyl-4'-nitro-2-morpholino acetanilide (A) Preparation of 2-propylamino-5-nitrobenzophenone In a manner similar to that described in Example 1(A) but using propylamine, one obtains 2-propylamino-5-nitrobenzophenone in a yield of 85%. Melting point: 150° C. Yellow crystals.

Slab chromatography:

support: silica gel 60 F 254 Merck; solvent: ethyl acetate/petroleum ether 10:90; development; UV and iodine; Rf: 0.4.

(B) Preparation of N-propyl-2'-benzoyl-4'-nitro-2-bromo acetanilide

In a manner similar to that described in Example 1(B) but using 2-N-propylamino-5-nitrobenzophenone, there is obtained, in a yield of 80%, N-propyl-2'-benzoyl-4'-nitro-2-bromo acetanilide. Pale yellow crystals. Melting point: 122° C.

Slab chromatography:

support: silica gel 60 F 254 Merck; solvent: ethyl acetate/petroleum ether 30:70; development: UV and iodine; Rf: 0.50.

(C) Preparation of the acid maleate of N-propyl-2'-benzoyl-4'-nitro-2-morpholino acetanilide In a manner similar to that described in Example 1(C) but using N-propyl-2'-benzoyl-4'-nitro-2-bromo acetanilide and maleic acid as salifying agent, there is obtained, in a yield of 75%, the product of the formula:

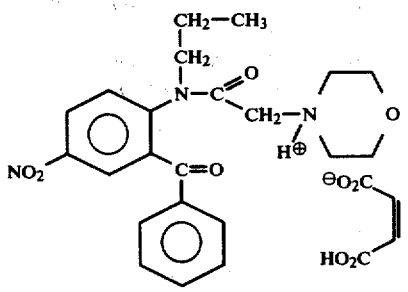

Empirical formula: $C_{26}H_{29}N_3O_9$;
Molecular weight: 527.54;
Crystals: White;
Melting point: 181° C.
Slab chromatography:
support: Silica gel 60 F 254 Merck; solvent: ethyl acetate; development: UV and iodine; Rf: 0.23.

EXAMPLE 4

Acid maleate of N-isopropyl-2'-benzoyl-4'-nitro-2-morpholino acetanilide (A) Preparation of 2-isopropylamino-5-nitrobenzophenone In a manner similar to that described in Example 1(A) but using isopropylamine, there is obtained, in a yield of 94%, 2-isopropylamino-5-nitrobenzophenone. Melting point: 155° C. Yellow crystals.

Slab chromatography:

support: silica gel 60 F 254 Merck; solvent: ethyl acetate/petroleum ether 10:90; development: UV and iodine; Rf: 0.18.

(B) Preparation of N-isopropyl-2'-benzoyl-4'-nitro-2-bromo acetanilide

In a manner similar to that described in Example 1(B) but using 2-isopropylamino-5-nitrobenzophenone there is obtained, in a yield of 95%, N-isopropyl-2'-benzoyl-4'-nitro-2-bromo acetanilide. Pale yellow oil.

Slab chromatography:

support: silica gel 60 F 254 Merck solvent: ethyl acetate/petroleum ether 30:70; development: UV and iodine; Rf: 0.50.

(C) Preparation of N-isopropyl-2'-benzoyl-4'-nitro-2-morpholino acetanilide

In a manner similar to that described in Example 1(C) but using N-isopropyl-2'-benzoyl-4'-nitro-2- bromo acetanilide and maleic acid as salifying agent, there is obtained in a yield of 85% the product of the formula:

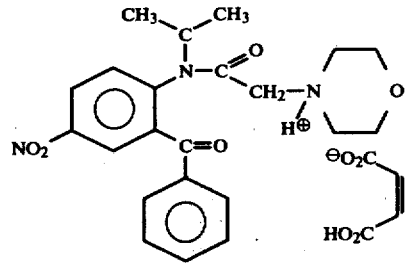

Empirical formula: $C_{26}H_{29}N_3O_9$; Molecular weight: 527.54; White crystals; Melting point: 183° C.

Slab chromatography:

support: silica gel 60 F Merck; solvent: ethyl acetate; development: UV and iodine; Rf: 0.32.

EXAMPLE 5

Maleate of N-allyl-2'-benzoyl-4'-nitro-2-morpholino acetanilide.

(A) Preparation of a 2-allyl-amino-5-nitrobenzophenone

In a manner similar to that described in Example 1(A) but using allylamine, there is obtained, in a yield of 95%, 2-allylamino-5-nitrobenzophenone. Melting point: 97° C. Yellow crystals.

Slab chromatography:

support: silica gel 60 F 254 Merck; solvent: ethyl acetate/petroleum ether 10:90; development: UV and iodine; Rf: 0.20.

(B) Preparation of N-allyl-2'-benzoyl-4'-nitro-2-bromo acetanilide

In a manner similar to that described in Example 1(B) but using 2-allylamino-5-nitrobenzophenone, there is obtained, in a yield of 91%, N-allyl-2'-benzoyl-4'-nitro-2-bromo acetanilide. Yellow oil.

Slab chromatography:

support: silica gel 60 F 254 Merck; solvent: ethyl acetate/petroleum ether 30:70; development: UV and iodine; Rf: 0.50.

(C) Preparation of acid maleate of N-allyl-2'-benzoyl-4'-nitro-2-morpholino acetanilide In a manner similar to that described in Example 1(C) but using N-allyl-2'-benzoyl-4'-nitro-2-bromo acetanilide and maleic acid as salifying agent, there is obtained, in a yield of 75%, the product of the formula:

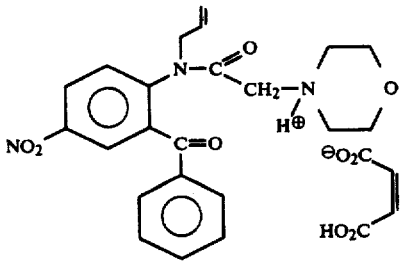

Empirical formula: $C_{26}H_{27}N_3O_9$; Molecular weight: 525.52; White crystals; Melting point: 165° C.

Slab chromatography:

support: silica gel 60 F 254 Merck; solvent: ethyl acetate; development: UV and iodine; Rf: 0.34.

EXAMPLE 6

N-benzyl-2'-benzoyl-4'-nitro-2-morpholino acetanilide

(A) Preparation of 2-benzylamino-5-nitro-benzophenone

In a manner similar to that described in Example 1(A) but using benzylamine there is obtained, in a yield of 70%, 2-benzylamino-5-nitrobenzophenone. Melting point: 120° C. Yellow crystals.

Slab chromatography:

support: silica gel 60 F 254 Merck; solvent: ethyl acetate/petroleum ether 10:90; development: UV and iodine; Rf: 0.22.

(B) Preparation of N-benzyl-2'-benzoyl-4'-nitro-2-bromo acetanilide

In a manner similar to that described in Example 1(B) but using 2-benzylamino-5-nitrobenzophenone there is obtained, in a yield of 94%, N-benzyl-2'-benzoyl-4'-nitro-2-bromo acetanilide. Melting point: 149° C., White crystals.

Slab chromatography:

support: silica gel 60 F 254 Merck; solvent: ethyl acetate/petroleum ether 30:70; development: UV and iodine; Rf: 0.62.

(C) Preparation of N-benzyl-2'-benzoyl-4'-nitro-2-morpholino acetanilide

In a manner similar to that described in Example 1(C) but using N-benzyl-2'-benzoyl-4'-nitro-2-bromo acetanilide there is obtained, in a yield of 84%, the product of the formula:

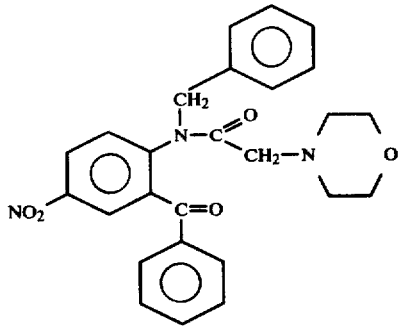

Empirical formula: $C_{26}H_{25}N_3O_5$; Molecular weight: 459.58; Crystals of a slightly colored white; Melting point: 110° C.

Slab chromatography:

support: silica gel 60 H 254 Merck; solvent: ethyl acetate; development: UV and iodine; Rf: 0.40.

EXAMPLE 7

N-cyclopropyl-2'-benzoyl-4'-nitro-2-morpholino acetanilide

(A) Preparation of 2-cyclopropylamino-5-nitrobenzophenone

In a manner similar to that described in Example 1(A) but using cyclopropylamine, there is obtained, in a yield of 65%, 2-cyclopropylamino-5-nitrobenzophenone. Yellow crystals. Melting point: 125° C.

Slab chromatography:

support: silica gel 60 F 254 Merck; solvent: ethyl acetate/petroleum ether 30:70; development UV and iodine; Rf: 0.70.

(B) Preparation of N-cyclopropyl-2'-benzoyl-4'-nitro-2-morpholino acetanilide In a manner similar to that described in Examples 1(B) and 1(C) but using 2-cyclopropylamino-5-nitrobenzophenone and then N-cyclopropyl-2'-benzoyl-4'-nitro-2-bromo acetanilide, there is obtained the product of the formula:

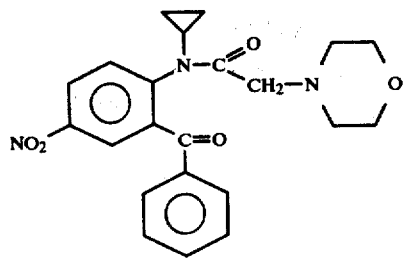

EXAMPLE 8

N-cyclopentyl-2'-benzoyl-4'-nitro-2-morpholino acetanilide (A) Preparation of 2-cyclopentylamino-5-nitrobenzophenone In a manner similar to that described in Example 1(A) but using cyclopentylamine there is obtained, in a yield of 82%, 2-cyclopentylamino-5-nitrobenzophenone. Yellow crystals. Melting point: 95° C.

Slab chromatography:

support: silica gel 60 F 254 Merck; solvent: ethyl acetate-petroleum ether 30:70; development: UV and iodine; Rf: 0.62.

(B) Preparation of N-cyclopentyl-2'-benzoyl-4'-nitro-2-morpholino acetanilide

In a manner similar to that described in Examples 1(B) and 1(C), but using 2-cyclopentylamino-5-nitrobenzophenone and N-cyclopentyl-2'-benzoyl-4'-nitro-2-bromo acetanilide, there is obtained the product of the formula:

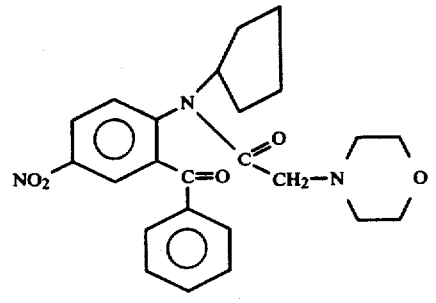

EXAMPLE 9

N-cyclohexyl-2'-benzoyl-4'-nitro-2-morpholino acetanilide (A) Preparation of 2-cyclohexylamino-5-nitrobenzophenone In a manner similar to that described in Example 1(A) but using cyclohexylamine, there is obtained, in a yield of 80%, 2-cyclohexylamino-5-nitrobenzophenone. Yellow crystals. Melting point: 75° C.

Slab chromatography:

support: silica gel 60 F 254 Merck; solvent: ethyl acetate/petroleum ether 30:70; development: UV and iodine; Rf: 0.63.

(B) Preparation of N-cyclohexyl-2'-benzoyl-4'-nitro-2-morpholino acetanilide

In a manner similar to that described in Example 1(B) and 1(C) but using 2-cyclohexylamino-5-nitrobenzophenone and N-cyclohexyl-2'-benzoyl-4'-nitro-2-bromo acetanilide, there is obtained the product of the formula:

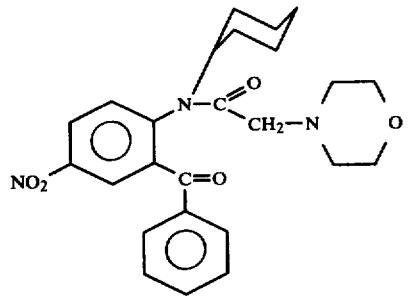

EXAMPLE 10

N-cyclohexyl-N'-methyl-2'-benzoyl-4'-nitro glycylanilide hydrochloride

To a solution of 3.77 g (0.01 mol) of N-methyl-2'-benzoyl-4'-nitro-2-bromo acetanilide in 40 cc of methylene chloride there is added 2.4 cc (0.021 mol) of cyclohexylamine, followed by heating for one hour under reflux. The organic phase is evaporated to dryness and the residue dissolved by ethyl acetate and then extracted 3 times with 50 cc of 6 N hydrochloric acid.

Aqueous phases are combined and treated with sodium carbonate and extracted with ethyl acetate. They are settled, washed with water and dried over sodium sulfate.

After filtration and evaporation of the ethyl acetate, there is recovered an oil, which is treated with a saturated ethanolic solution of hydrochloric acid. After recrystallization from ethanol, there is recovered, in a yield of 70%, the product of the formula:

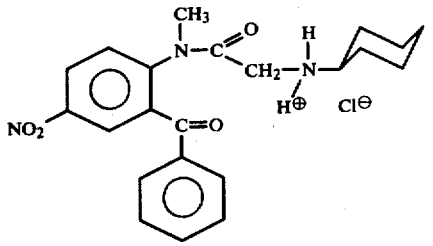

Empirical formula: $C_{22}H_{26}ClN_3O_4$; Molecular weight: 431.9; Crystals: white; Melting point: 204° C.

Slab chromatography:

support: silica gel 60 F 254 Merck; solvent: butanol-/acetic-acid/water 6:2:2; development;: UV and iodine; Rf: 0.43.

EXAMPLE 11

Fumarate of
N,N'-dimethyl-N-cyclohexyl-2'-benzoyl-4'-nitro glycylanilide

In a manner similar to that described in Example 10 but using N-methyl-cyclohexylamine and fumaric acid as salifying agent, there is obtained, in a yield of 65%, the product of the formula:

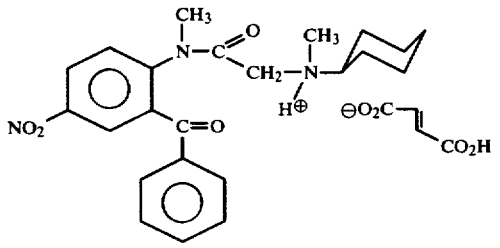

Empirical formula: $C_{27}H_{31}N_3O_8$: Molecular weight: 525.56; Crystals: white; Melting point: 173° C.

Slab chromatography: support: silica gel 60 F 254 Merck; solvent: butanol/acetic-acid/water 6:2:2; development: UV and iodine; Rf: 0.39.

EXAMPLE 12

N'-methyl-N-cyclopropyl-2'-benzoyl-4'-nitro glycylanilide

In a manner similar to that described in Example 10, but using cyclopropylamine, there is obtained the product of the formula:

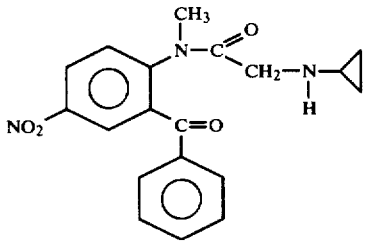

EXAMPLE 13

N'-methyl-N-1,1-dimethyl-propargyl-2'-benzoyl-4'-nitro glycylanilide

In a manner similar to that described in Example 10, but using 1,1-dimethyl propargylamine, there is obtained the product of the formula:

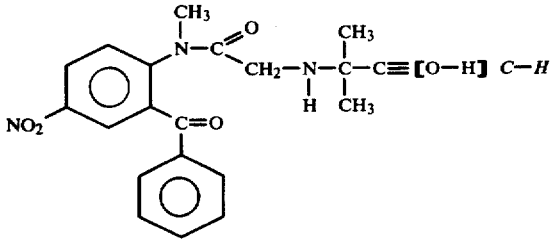

EXAMPLE 14

N'-methyl-N-allyl-2'-benzoyl-4'-nitroglycylanilide

In a manner similar to that described in Example 10, but using allylamine, there is obtained the product of the formula:

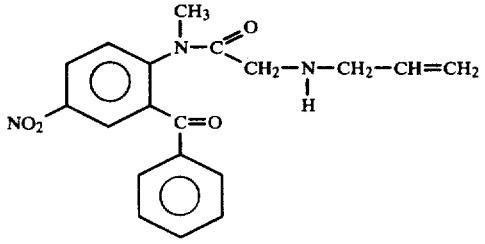

EXAMPLE 15

N,N'-dimethyl-N-(2-hydroxyethyl)-2'-benzoyl-4'-nitro glycylanilide

In a manner similar to that described in Example 10, but using N-methyl ethanolamine, there is obtained the product of the formula:

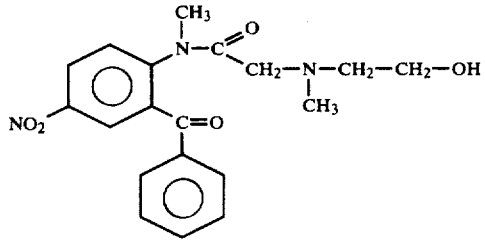

EXAMPLE 16

N'-methyl-N,N-bis-(2-hydroxyethyl)-2'-benzoyl-4'-nitro glycylanilide

In a manner similar to that described in Example 10, but using diethanolamine, there is obtained the product of the formula:

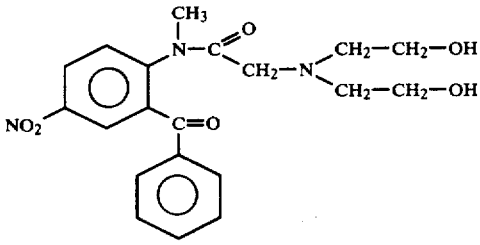

EXAMPLE 17

N-methyl-2-(4'-methyl piperazino)-(2-benzoyl-4'-nitro)acetanilide

In a manner similar to that described in Example 10, but using N-methyl piperazine, there is obtained the product of the formula:

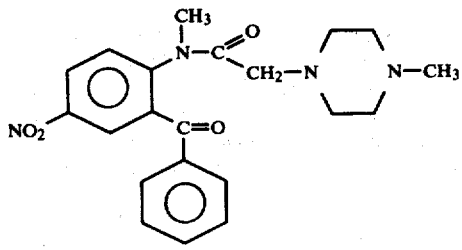

The compounds of the present invention, which have a remarkable action on the central nervous system, are therefore capable of being administered to man or animal orally or by injection, in the form of a free base or else in the form of one of their therapeutically acceptable salts.

By way of simple illustration, there are indicated below a few results of various toxicological and pharmacological tests carried out on the chemical compounds of the invention.

PHARMACOLOGICAL PROPERTIES (A) Tests Used (1) Toxicity Study

The compounds of the present invention were subjected to toxicity controls. The $LD_{50}$ is between 500 and 3000 mg/kg for all the derivatives tested. It was determined orally and calculated in accordance with the method of Miller and Tainter (Proc. Soc. exper. Biol. Med., 1944, 57, 261).

(2) Activity in the Rotarod Test

This test was carried out on male mice of Swiss strain. The mouse was placed on a wooden rod of a diameter of 3 cm rotating at the rate of 5 revolutions per minute. The mice who are able to remain on the rod for at least three minutes during the course of successive tests are selected and assembled in groups of 10 for the testing of each dose. If the mouse falls from the rod in less than two minutes, the compound tested is considered effective.

The results of the compounds are expressed as $ED_{50}$ in accordance with N. W. Dunham and T. S. Miva—J. Amer. Pharm. Assoc., 1957, 46, 208. The $ED_{50}$ values of the compounds of greatest interest vary from 0.2 to 20 mg/kg.

(3) Anti-pentetrazol activity

This test was carried out on a group of 10 male mice of Swiss strain. Within a period of 15 minutes after the subcutaneous injection of 125 mg/kg of penetrazol, the mice have tonic convulsions the outcome of which is fatal. For the test, the compounds are administered orally 60 minutes before the injection of pentetrazol. The animals are observed for two hours after administration of the pentetrazol.

The results are expressed by the effective dose $ED_{50}$ in accordance with Goodmann et al. J. Pharmacol. 108,1953. The $ED_{50}$ values of the most interesting compunds vary from 0.1 to 3 mg/kg.

THERAPEUTIC APPLICATIONS

In view of their pharmacological properties and their low toxicity, these chemical compounds can be used in therapy and, more particularly, for the treatment of insomnia.

These compounds and their therapeutically compatible acid addition salts can be used as drugs, for instance in the form of pharmaceutical preparations suitable for enteral or parenteral administration with, for instance, water, lactose, gelatin, starches, magnesium stearate, talc, vegetable oils, gums, polyalkylene glycols, petroleum jelly, etc.

These preparations may be in solid form, for instance in the form of tablets, pills, capsules, etc., or else in liquid form, for instance solutions, suspensions or emulsions.

The pharmaceutical preparations in a form suitable for injection are preferred. These preparations can be subjected to conventional pharmaceutical operations such as sterilization and/or may contain adjuvants, for instance preservatives, stabilizers, wetting or emulsifying agents, buffer compounds, etc.

The doses in which the active compounds and their therapeutically compatible acid addition salts can be administered may vary within large proportions depending on the condition of the patient. A daily dose of about 0.01 mg to 1 mg per kg of body weight is, however, preferred.

The pharmaceutical compositions of the invention can be used in medicine, for instance in the treatment of insomnia. Such compositions may furthermore contain other active principles which supplement or reinforce the therapeutic action of the derivatives of general formula I of the present invention.

Of course, the present invention is not limited to the particular examples, which have been given merely by way of illustration, but it is entirely possible, without thereby going beyond the scope of the inveniton, to devise a number of variants and modifications thereof.

What is claimed is:

1. 2-benzoyl-4-nitro anilides having the formula I:

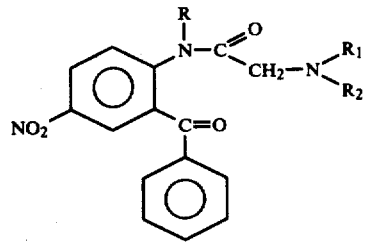

in which

R represents alkyl, alkenyl, cycloalkyl, or benzyl;

$R_1$ represents hydrogen, alkyl or hydroxyalkyl;

$R_2$ represents hydroxyalkyl, alkenyl or alkynyl, unsubstituted or substituted one or more times by an alkyl radical, or cycloalkyl having three to six carbon atoms, inclusive;

$R_1$ and $R_2$ may furthermore form, with the nitrogen atom to which they are attached, a nitrogen heterocycle which may also contain a second heteroatom selected from oxygen and nitrogen;

provided, however that, when $R_2$ represents hydroxyalkyl, $R_1$ may not be hydrogen, as well as their salts obtained with therapeutically acceptable inorganic or organic acids.

2. Compounds of formula I in accordance with claim 1, characterized by the fact that they are selected from among N-methyl-2'-benzoyl-4'-nitro-2-morpholino acetanilide hydrochloride, acid maleate of N-ethyl-2'-benzoyl-4'-nitro-2-morpholino acetanilide, acid maleate of N-propyl-2'-benzoyl-4'-nitro-2-morpholino acetanilide.

acid maleate of N-isopropyl-2'-benzoyl-4'-nitro-2-morpholino acetanilide.

maleate of N-allyl-2'-benzoyl-4'-nitro-2-morpholino acetanilide,

N-benzyl-2'-benzoyl-4'-nitro-2- morpholino acetanilide,

N-cyclopropyl-2'-benzoyl-4'-nitro-2-morpholino acetanilide,

N-cyclopentyl-2'-benzoyl-4'-nitro-2-morpholino acetanilide,

N-cyclohexyl-2'-benzoyl-4'-nitro-2-morpholino acetanilide,

N-cyclohexyl-N'-methyl-2'-benzoyl-4'-nitro glycylanilide hydrochloride,

N,N'-dimethyl-N-cyclohexyl-2'-benzoyl-4'-nitro-glycylanilide fumarate;

N'-methyl-N-cyclopropyl-2'-benzoyl-4'-nitro-glycylanilide,

N'-methyl-N-1,1-dimethyl propargyl 2'-benzoyl-4'-nitro glycylanilide,

N'-methyl-N-allyl-2'-benzoyl-4'-nitro glycylanilide,

N,N'-dimethyl-N-(2-hydroxy ethyl)-2'-benzoyl-4'-nitro-glycylanilide,

N'-methyl-N,N-bis-(2-hydroxy ethyl)-2'-benzoyl-4'-nitro glycylanilide, and

N-methyl-2-(4'-methylpiperazino)-(2'-benzoyl-4'-nitro) acetanilide.

3. A compound of claim 1 selected from the group consisting of 2'-benzoyl-4'-nitro-2-morpholinoacetanilides and the pharmaceutically-acceptable acid addition salts thereof, having an N-substituent selected from the group consisting of lower-alkyl, lower-alkenyl, benzyl, and cycloalkyl having a maximum of six (6) carbon atoms in the ring.

4. A compound of claim 1 selected from the group consisting of 2'-benzoyl-4'-nitro-glycylanilides, and the pharmaceutically-acceptable acid addition salts thereof, having one N-substituent selected from the group consisting of lower-alkenyl, cycloalkyl having a maximum of six (6) carbon atoms in the ring, lower-alkynyl, and hydroxylower-alkyl, and having the other N-substituent selected from hydrogen, lower alkyl and hydroxy lower alkyl and having an N'-substituent which is lower-alkyl.

5. A pharmaceutical composition suitable for use as a hypnotic comprising an effective hypnotic amount of a compound of claim 1 or claim 2 in combination with a pharmaceutically acceptable carrier or adjuvant.

6. Method for the treatment of a subject suffering from insomnia, comprising the step of administering to the said subject an effective hypnotic amount of a compound of claim 1 or 2.

* * * * *